(12) United States Patent
Ohishi et al.

(10) Patent No.: US 8,217,150 B2
(45) Date of Patent: Jul. 10, 2012

(54) TOXIN DETECTION METHOD

(75) Inventors: Kanenari Ohishi, Niigata (JP); Tadashi Baba, Tokyo (JP); Keiichi Hiramatsu, Tokyo (JP); Yasuo Nakatomi, Niigata (JP)

(73) Assignees: Juntendo University School of Medicine, Tokyo (JP); Denka Seiken Co., Ltd., Tokyo (JP)

( * ) Notice: Subject to any disclaimer, the term of this patent is extended or adjusted under 35 U.S.C. 154(b) by 0 days.

(21) Appl. No.: 13/113,276

(22) Filed: May 23, 2011

(65) Prior Publication Data

US 2011/0223614 A1 Sep. 15, 2011

Related U.S. Application Data

(62) Division of application No. 12/306,863, filed as application No. PCT/JP2007/063278 on Jul. 3, 2007, now Pat. No. 7,947,808.

(30) Foreign Application Priority Data

Jul. 3, 2006 (JP) ................................. 2006-183535

(51) Int. Cl.
*C07K 16/00* (2006.01)
(52) U.S. Cl. ............... 530/387.1; 530/388.1; 530/388.2; 530/389.5; 435/975
(58) Field of Classification Search .................. None
See application file for complete search history.

(56) References Cited

U.S. PATENT DOCUMENTS

| 7,947,808 B2 * | 5/2011 | Ohishi et al. ............... 530/387.1 |
| 2008/0131457 A1 | 6/2008 | Taylor et al. |
| 2009/0074755 A1 | 3/2009 | Taylor et al. |

FOREIGN PATENT DOCUMENTS

| JP | 2000-316574 | 11/2000 |
| JP | 2000316574 | * 11/2000 |
| WO | WO 2006/078213 A1 | 7/2006 |
| WO | WO 2006/135912 A2 | 12/2006 |

OTHER PUBLICATIONS

Rainard et al (Clinical and Diagnostic Laboratory Immunology vol. 18, No. 2, pp. 272-277, Mar. 2003).*
Arifur Rahman et al., "Gamma-Hemolysin Genes in the Same Family with LukF and lukS Genes in Methicillin Resistant *Staphylococcus aureus*", Biosci. Biotech. Biochem. 57(7), 1234-1236, 1993.
Communication Pursuant to Article 94(3)EPC European Application No. 07 768 052.8-2406 dated Jan. 23, 2012.
Non-final office action U.S. Appl. No. 12/306,863 dated Jul. 15, 2010.
Gershon et al., Immunofluorescent Demonstration of Leucocidin Components, pp. 477-495 (1968).
Non-final office action U.S. Appl. No. 12/306,863 dated May 7, 2010.
Non-final office action U.S. Appl. No. 12/306,863 dated Apr. 28, 2010.
Notice of Allowance U.S. Appl. No. 12/306,863 dated Jan. 18, 2011.
V. Finck-Barbancon et al., "Improved purification of leukocidin from *Staphylococcus aureus* and toxin distribution among hospital strains", Res. Microbiol. 1991, 142, 75-85.
Valerie Gauduchon et al., "Neutralization of *Staphylococcus aureus* Panton Valentine Leukocidin by Intravenous Immunoglobulin In Vitro", JID, Jan. 15, 2004:189 pp. 346-353.
A. Gravet D.A. et al., "Characterization of a novel structural member, LukE-LukD, of the bi-component staphylococcal leucotoxins family", FEBS Letters, 436 (1998) 202-208.
G. Prevost et al., "Panton-Valentine Leucocidin and Gamma-Hemolysin from *Staphylococcus aureus* ATCC 49775 Are Encoded by Distinct Genetic Loci and Have Different Biological Activities", Infection and Immunity, Oct. 1995, vol. 63, No. 10, pp. 4121-4129.
Wanna Choorit et al., "Existence of a new protein component with the same function as the LukF component of leukocidin or γ-hemolysin and its gene in *Staphylococcus aureus* P83", FEBS Letters 357 (1995) 260-264.
Pascal Rainard et al., "Leucotoxic Activities of *Staphylococcus aureus* Strains Isolated from Cows, Ewes, and Goats with Mastitis: Importance of LukM/LukF'-PV Leukotoxins", Clinical and Diagnostic Laboratory Immunology, Mar. 2003, vol. 10, No. 2, pp. 272-277.
Supplementary European Search Report EP 07 76 8052 dated Jul. 14, 2010.
Kanenari Oishi et al., "A latex agglutination assay for specific detection of Panton-Valentine leukocidin", Journal of Microbiological Methods, 75 (2008) pp. 411-415.
G. Prevost et al., "Epidemiological data on *Staphylococcus aureus* strains producing synergohymenotropic toxins", J. Med. Microbiol.—vol. 42 (1995) 237-245.

* cited by examiner

*Primary Examiner* — Albert Navarro

(74) *Attorney, Agent, or Firm* — Stephen A Bent; Foley & Lardner LLP

(57) ABSTRACT

According to the present invention, an antibody against a Panton-Valentine leukocidin toxin contained in *Staphylococcus aureus*, a method and a kit for detecting the toxin with the use of the antibody, and a pharmaceutical composition containing an antibody against a Panton-Valentine leukocidin toxin for treating PVL infection caused by *Staphylococcus aureus* containing PVL are provided. Also, an antibody which is capable of binding to Panton-Valentine leukocidin F and has no cross-reactivity to LukD and/or HlgB and an antibody which is capable of binding to Panton-Valentine leukocidin S and has no cross-reactivity to at least one of LukE, HlgC, and HlgA are provided.

4 Claims, 4 Drawing Sheets

Fig. 1

| Strain name (PVL-gene-positive strain) | Presence or absence of PVL gene (PCR) | Strain name (PVL-gene-negative strain) | Presence or absence of PVL gene (PCR) |
|---|---|---|---|
| C199800370 | + | MW2 ΔPVL | − |
| C199900529 | + | N315 | − |
| C1999000193 | + | JCSC2952 | − |
| C1999000459 (MW2) | + | JCSC2962 | − |
| C2001001201 | + | M9N | − |
| C2001000101 | + | M33T | − |
| C200100818 | + | W1S | − |
| JCSC5174 | + | C7N | − |
| JCSC5182 | + | 00215 | − |
| JCSC5183 | + | 01093 | − |
| JCSC5184 | + | 81 0342 | − |
| JCSC5192 | + | 81 0508 | − |
| JCSC5391 | + | 81 0937 | − |
| JCSC5169 | + | 81 1238 | − |
| JCSC5170 | + | 91 1573 | − |
| JCSC5171 | + | 91 1575 | − |
| JCSC5172 | + | 91 1703 | − |
| JCSC5189 | + | 91 2118 | − |
| JCSC108 | + | 91 2125 | − |
| JCSC2911 | + | 91 2145 | − |
| JCSC2912 | + | 91 2231 | − |
| JCSC2913 | + | 91 2572 | − |
| JCSC2914 | + | 91 2574 | − |
| JCSC4488 | + | 91 2619 | − |
| ATCC49775 | + | 91 2666 | − |
| 01083 | + | SAP260 | − |
| 01102 | + | SAP344 | − |
| A80 3355 | + | SAP411 | − |
| A82 3549 | + | WCH379 | − |
| A83 0528 | + | | |
| B82 6559 | + | | |
| D82 1552 | + | | |
| E80 2537 | + | | |
| F81 0539 | + | | |
| I80 2552 | + | | |

Fig. 2A

| Strain name (PVL-gene-positive strain) | PVL gene | Determination for PVL detection (the present method) | Sensitized latex F (endpoint titer) | Sensitized latex S (endpoint titer) |
|---|---|---|---|---|
| C199800370 | + | + | >1:128 | >1:128 |
| C199900529 | + | + | >1:128 | >1:128 |
| C1999000193 | + | + | 1:64 | >1:128 |
| C1999000459 (MW2) | + | + | >1:128 | >1:128 |
| C2001001201 | + | + | >1:128 | >1:128 |
| C2001000101 | + | + | >1:128 | >1:128 |
| C200100818 | + | + | >1:128 | >1:128 |
| JCSC5174 | + | + | >1:128 | >1:128 |
| JCSC5182 | + | + | >1:128 | 1:32 |
| JCSC5183 | + | + | >1:128 | >1:128 |
| JCSC5184 | + | + | >1:128 | >1:128 |
| JCSC5192 | + | + | >1:128 | >1:128 |
| JCSC5391 | + | + | >1:128 | >1:128 |
| JCSC5169 | + | + | >1:128 | >1:128 |
| JCSC5170 | + | + | >1:128 | >1:128 |
| JCSC5171 | + | + | >1:128 | >1:128 |
| JCSC5172 | + | + | >1:128 | >1:128 |
| JCSC5189 | + | + | >1:128 | >1:128 |
| JCSC108 | + | + | 1:16 | 1:8 |
| JCSC2911 | + | + | >1:128 | >1:128 |
| JCSC2912 | + | + | >1:128 | >1:128 |
| JCSC2913 | + | + | >1:128 | >1:128 |
| JCSC2914 | + | + | >1:128 | >1:128 |
| JCSC4488 | + | + | >1:128 | >1:128 |
| ATCC49775 | + | + | 1:32 | 1:16 |
| 01083 | + | + | >1:128 | >1:128 |
| 01102 | + | + | >1:128 | >1:128 |
| A80 3355 | + | + | 1:128 | 1:32 |
| A82 3549 | + | + | 1:128 | 1:32 |
| A83 0528 | + | + | >1:128 | 1:64 |
| B82 6559 | + | + | 1:128 | 1:32 |
| D82 1552 | + | + | >1:128 | 1:64 |
| E80 2537 | + | + | >1:128 | 1:64 |
| F81 0539 | + | + | 1:128 | 1:32 |
| I80 2552 | + | + | 1:32 | 1:16 |

Fig. 2B

| Strain name (PVL-gene-positive strain) | PVL gene | Determination for PVL detection (the present method) | Sensitized latex F (endpoint titer) | Sensitized latex S (endpoint titer) |
|---|---|---|---|---|
| MW2 ΔPVL | − | − | <1:2 | <1:2 |
| N315 | − | − | <1:2 | <1:2 |
| JCSC2952 | − | − | <1:2 | <1:2 |
| JCSC2962 | − | − | <1:2 | <1:2 |
| M9N | − | − | <1:2 | <1:2 |
| M33T | − | − | <1:2 | <1:2 |
| W1S | − | − | <1:2 | <1:2 |
| C7N | − | − | <1:2 | <1:2 |
| 00215 | − | − | <1:2 | <1:2 |
| 01093 | − | − | <1:2 | <1:2 |
| 81 0342 | − | − | <1:2 | <1:2 |
| 81 0508 | − | − | <1:2 | <1:2 |
| 81 0937 | − | − | <1:2 | <1:2 |
| 81 1238 | − | − | <1:2 | <1:2 |
| 91 1573 | − | − | <1:2 | <1:2 |
| 91 1575 | − | − | <1:2 | <1:2 |
| 91 1703 | − | − | <1:2 | <1:2 |
| 91 2118 | − | − | <1:2 | <1:2 |
| 91 2125 | − | − | <1:2 | <1:2 |
| 91 2145 | − | − | <1:2 | <1:2 |
| 91 2231 | − | − | <1:2 | <1:2 |
| 91 2572 | − | − | <1:2 | <1:2 |
| 91 2574 | − | − | <1:2 | <1:2 |
| 91 2619 | − | − | <1:2 | <1:2 |
| 91 2666 | − | − | <1:2 | <1:2 |
| SAP260 | − | − | <1:2 | <1:2 |
| SAP344 | − | − | <1:2 | <1:2 |
| SAP411 | − | − | <1:2 | <1:2 |
| WCH379 | − | − | <1:2 | <1:2 |

Fig. 3

|  | | PCR | |  |
|---|---|---|---|---|
|  | | Positive | Negative |  |
| The present method | Positive | 35 | 0 | 35 |
|  | Negative | 0 | 29 | 29 |
|  | | 35 | 29 | 64 |

Match rate (Positive)   : 100%

Match rate (Negative)   : 100%

Match rate              : 100%

Non-match rate          :   0%

Hitting rate (Positive) : 100%

Hitting rate (Negative) : 100%

TOXIN DETECTION METHOD

CROSS REFERENCE TO RELATED APPLICATIONS

This application is a divisional application of U.S. application Ser. No. 12/306,863 filed Dec. 29, 2008, which is the U.S. National Phase of PCT/JP2007/063278 filed Jul. 3, 2007, which claims priority from Japanese Patent Application No. 2006-183535 filed Jul. 3, 2006. Each application is incorporated herein in its entirety.

TECHNICAL FIELD

The present invention relates to an antibody specific to a bacterial-produced antigenic substance, especially such as a protein, peptide, or protein toxin, and also relates to a toxin detection method using the same.

More specifically, the present invention relates to an antibody against a protein toxin produced by *Staphylococcus aureus*.

Further specifically, the present invention relates to an antibody specific to Panton-Valentine leukocidin (hereinafter referred to as "PVL"), which is a binary toxic protein (two-component toxic protein) produced by *Staphylococcus aureus*.

Furthermore, the present invention relates to a method and a kit for detecting PVL, which is a toxic protein produced by *Staphylococcus aureus*, with the use of the above antibody.

Moreover, the present invention relates to a method wherein the above artificial antibody is used as an antitoxin vaccine or an antitoxin neutralizing antibody. Further specifically, the present invention relates to a method for preventing PVL infection by administering an anti-PVL antibody and a method for treating PVL infection by administering an anti-PVL antibody.

BACKGROUND ART

*Staphylococcus aureus* is a facultative anaerobic Gram-positive coccus. It is a microorganism widely distributed in nature and causes both nosocomial and opportunistic infection. It is recognized as a main causative bacterium that induces, for example, food poisoning accompanied by pyelitis, cystitis, impetigo, localized abscess, osteomyelitis, sepsis, and/or vomiting.

In addition, as a type of *Staphylococcus aureus*, Methicillin-resistant *Staphylococcus aureus* (MRSA) has been found, which results from chromosomal variation and thus is highly resistant to a variety of antibiotics. MRSA proliferates in persons with compromised immune systems such as elderly persons, newborn infants, and cancer patients so as to cause pneumonia, sepsis, and the like, resulting in death in some cases.

Since MRSA was first reported in England in 1961, MRSA has been known as a bacterium causing nosocomial infection. However, in 1981, an MRSA infection case (community-acquired MRSA), which was not a nosocomial infection case, was reported in the U.S. (see Non-Patent Document 1). Hitherto, many cases of non-nosocomial infections confirmed with MRSA via isolation have been reported all over the world.

Community-acquired MRSA is known to have a bacteriological feature of having a high probability of having a gene encoding PVL that is a leukocytolytic toxin (see Non-Patent Document 2).

The PVL toxin is characterized in that it is a binary toxin comprising two proteins, which are Panton-Valentine leukocidin F (hereinafter referred to as "LukF-PV") and Panton-Valentine leukocidin S (hereinafter referred to as "LukS-PV"). PVL itself does not have toxic activity; however, it exhibits cytolytic activity specific to leukocytic cells when the two components function in combination.

From 1997 to 1999, deaths from childhood pneumonia/sepsis caused by community-acquired MRSA having the PVL gene were reported in succession in Minnesota and North Dakota in the U.S. (see Non-Patent Document 3). The importance of PVL detection from community-acquired MRSA has been gaining attention. Further, in addition to MRSA, the importance of PVL detection from *Staphylococcus aureus* has also been gaining attention.

At present, PVL gene detection by the PCR method has been carried out as a PVL detection method (see Non-Patent Documents 4 and 5).

In addition to the above, G. PREVOST et al. produced an antibody against the PVL toxin and they reported an example of immunological detection of the PVL toxin with the use of the antibody (see Non-Patent Document 6).

Further, a method for controlling *Staphylococcus aureus* with the use of antibiotics or an antibacterial agent has so far been available. However, a method for directly preventing or treating a disorder caused by PVL produced by *Staphylococcus aureus* has not been established.

Non-Patent Document 1: CDC (Centers for Disease Control) in the U.S.: "Community-acquired methicillin-resistant *Staphylococcus aureus* infections-Michigan" Morbidity and Mortality Weekly Report, 1981; Vol. 30, pp. 185-187

Non-Patent Document 2: "Community-acquired MRSA gene structure and diagnosis (findings in bacteria)" written by Teruyo Ito et al., The Journal of the Japanese Association for Infectious Diseases, June in 2004, vol. 78, no. 6, pp. 459-469

Non-Patent Document 3: CDC (Centers for Disease Control) in the U.S.: "Four pediatric deaths from community-acquired methicillin-resistant *Staphylococcus aureus*" Morbidity and Mortality Weekly Report, 1999; Vol. 48, pp. 707-710

Non-Patent Document 4: "Involvement of Panton-Valentine leukocidine-producing *Staphylococcus aureus* in primary skin infections and pneumonia" written by Lina G, Piemont, Godial-Gamot F. et al., Clinical infectious Diseases, 1999; Vol. 29, pp. 1128-1132

Non-Patent Document 5: "The emergence of Panton-Valentine leukocidin-positive community-acquired Methicillin-resistant *Staphylococcus aureus*" written by Tatsuo Yamamoto et al., Japanese Journal of Chemotherapy, November in 2004, Vol. 52, pp. 635-653

Non-Patent Document 6: "Characterization of a novel structural member, LukE-LukD, of the bi-component staphylococcal leucotoxins family" written by A. Gravet, G. Prevost et al., FEBS Letters, 1998, Vol. 436, pp. 202-208

DISCLOSURE OF THE INVENTION

Problem to be Solved by the Invention

A method for amplifying and detecting the PVL gene by the PCR method, which is currently used as a PVL detection method, requires appropriate facilities and well-experienced technicians. Further, it is time-consuming to use such method to obtain results and thus it is not a rapid method, which is problematic. Moreover, one PVL detection method reported as an immunological method is problematic in terms of specificity. Thus, the existing assay methods are problematic in terms of reliability.

It is an objective of the present invention to solve the above problems and to provide antibodies specific to LukF-PV and LukS-PV, an assay method whereby one or two types of target substances can be detected in a specific manner, and an assay kit for the method.

It is another objective of the present invention to provide an anti-PVL antibody, a method for preventing PVL infection by administering the anti-PVL antibody, and a method for preventing PVL infection by administering the anti-PVL antibody so as to prevent or treat a PVL-caused disorder.

Means for Solving Problem

PVL is a binary toxin composed of the two proteins LukF-PV and LukS-PV.

When rabbits or mice are immunized with LukF-PV as an antigen, a polyclonal antibody or monoclonal antibody against LukF-PV can be obtained. In addition, when rabbits or mice are immunized with LukS-PV as an antigen, a polyclonal antibody or monoclonal antibody against LukS-PV can be obtained.

There are genes known to be homologous to the genes encoding the above components of PVL, including: the leukocidin D gene and the leukocidin E gene, each of which encodes a PVL variant; and the γ-hemolysin A gene, the γ-hemolysin B gene, and the γ-hemolysin C gene, each of which encodes a γ-hemolysin (hereinafter proteins encoded by the above genes are referred to as "LukD," "LukE," "HlgA," "HlgB," and "HlgC," respectively). In the case of a conventional detection method using an antibody against LukF-PV or LukS-PV, it is unclear whether LukF-PV or LukS-PV is detected in a specific manner.

As a result of intensive studies to solve the above problems, the present inventors have found that an antibody specific to LukF-PV or LukS-PV can be produced by treating the above polyclonal antibody obtained as a result of immunization with LukF-PV or LukS-PV to remove by absorption the reactivity to proteins genetically homologous to LukF-PV or LukS-PV (the LukF-PV homologous proteins LukD and HlgB or the LukS-PV homologous proteins LukE, HlgC, and HlgA).

In addition, they have found that a monoclonal antibody, which is obtained as a result of immunization with LukF-PV or LukS-PV, has no reactivity to proteins genetically homologous to LukF-PV or LukS-PV (the LukF-PV homologous proteins LukD and HlgB or the LukS-PV homologous proteins LukE, HlgC, and HlgA).

That is, it is an objective of the present invention to provide an antibody specific to LukF-PV or LukS-PV and to provide a kit for specific and highly sensitive assay of the relevant substance with the use of such an antibody.

Specific and highly sensitive detection of PVL (LukF-PV and LukS-PV) has been achieved by detecting LukF-PV and/or LukS-PV by an immunoassay method such as a labeling immunoassay method wherein the above specific antibody is labeled for use, a method using an antigen-antibody agglutination reaction with the specific antibody, or immunochromatography.

In addition, as a result of intensive studies, the present inventors have found an antibody capable of inhibiting the leukocytolytic toxin activity of PVL. Thus, it has become possible to prevent a PVL infection by administering the antibody and to treat a PVL infection by administering an anti-PVL antibody.

Specifically, the present invention is described as follows.

[1] An antibody which is capable of binding to Panton-Valentine leukocidin F and has no cross-reactivity to LukD and/or HlgB.

[2] An antibody which is capable of binding to Panton-Valentine leukocidin S and has no cross-reactivity to at least one of LukE, HlgC, and HlgA.

[3] An antibody capable of inhibiting leukocytolytic toxin activity of Panton-Valentine leukocidin.

[4] An antibody which is capable of binding to Panton-Valentine leukocidin F so as to inhibit leukocytolytic toxin activity and has no cross-reactivity to LukD and/or HlgB.

[5] An antibody which is capable of binding to Panton-Valentine leukocidin S so as to inhibit leukocytolytic toxin activity and has no cross-reactivity to at least one of LukE, HlgC, and HlgA.

[6] The antibody according to any one of [3] to [5], which is a Panton-Valentine-leukocidin-toxin-neutralizing antibody.

[7] A Panton-Valentine leukocidin detection kit comprising the antibody according to any one of [1] to [5].

[8] A method for detecting a Panton-Valentine leukocidin toxin, comprising allowing the antibody according to any one of [1] to [5] to come into contact with a culture product of *Staphylococcus aureus*.

[9] A pharmaceutical composition containing at least one antibody selected from among the antibodies according to [3] to [5].

[10] An anti-Panton-Valentine leukocidin toxin vaccine containing at least one antibody selected from among the antibodies according to [3] to [5].

Effects of the Invention

According to the present invention, a method whereby a PVL toxin protein can be detected with excellent specificity, high sensitivity, and high reliability in a convenient manner is provided. A PVL toxin protein is produced by *Staphylococcus aureus*. Specific and highly sensitive detection of the toxin protein is difficult with the use of conventional techniques, and it is very time-consuming to obtain detection results. Further, according to the present invention, a kit for detecting a PVL toxin protein produced by *Staphylococcus aureus* is provided. In a case in which a pathogenic factor is a toxin, it is important to detect the toxin protein thereof. With the use of a gene detection method, information regarding the probability of protein expression can be obtained as a result of detection of a target gene; however, it is impossible to know whether or not the expression is actually induced. According to the present invention, it has become possible to directly detect such toxin protein so as to provide protein-level information regarding the toxin protein as a pathogenic factor.

In addition, an anti-PVL antibody, a method for preventing a PVL infection by administering the anti-PVL antibody, and a method for treating a PVL infection by administering the anti-PVL antibody are provided.

This description includes part or all of the contents as disclosed in the description and/or drawings of Japanese Patent Application No. 2006-183535, which is a priority document of the present application.

BRIEF DESCRIPTION OF THE DRAWINGS

FIG. 1 shows a table listing the names of PVL-gene-positive *Staphylococcus aureus* strains and the names of PVL-gene-negative *Staphylococcus aureus* strains used in the present invention. The MW2ΔPVL strain is a strain obtained through PVL gene knockdown in the C1999000459 strain (MW2 strain), which is a PVL-gene-positive strain.

FIG. 2A shows a table listing results for detection of PVL contained in a specimen culture supernatant with the use of the reagent of the present invention. The table also lists endpoint titers at which an agglutination image obtained as a result of a reaction with the relevant sensitized latex is observed.

FIG. 2B shows a table listing results for detection of PVL contained in a specimen culture supernatant with the use of the reagent of the present invention (continued from FIG. 2A). The table also lists endpoint titers at which an agglutination image obtained as a result of a reaction with the relevant sensitized latex is observed. The MW2ΔPVL strain is a strain obtained through PVL gene knockdown in the C1999000459 strain (MW2 strain), which is a PVL-gene-positive strain FIG. 3 shows the correlation between PVL detection results obtained by the method of the present invention and PVL gene detection results obtained by the PCR method.

BEST MODE FOR CARRYING OUT THE INVENTION

Hereinafter, the method of the present invention is described in detail.

Antibodies

Examples of the antibody of the present invention include polyclonal antibodies and monoclonal antibodies produced with the use of chickens and mammalian animals such as rabbits, mice, rats, sheep, and goats. Also, the present invention encompasses humanized antibodies and human antibodies such as human monoclonal antibodies, human polyclonal antibodies, and recombinant human monoclonal antibodies. The term "humanized antibody" includes human chimeric antibodies and human CDR (Complementarity Determining Region; hereinafter referred to as "CDR")-transplanted antibodies. The term "human antibody" includes human antibody phage libraries produced by genetic engineering, cellular engineering, and developmental engineering techniques and antibodies obtained from human antibody-producing transgenic animals. Humanized antibodies and human antibodies can be produced by known methods. Further, monoclonal antibodies may be either complete antibodies or fragments comprising antibody binding sites such as Fab, Fab', F(ab')2, and Fv.

Preparation of Immunogens

PVL can be purified as an immunogen from PVL-producing *Staphylococcus aureus* by a known method (Infection AND Immunity, October, 1995, 4121-4129).

PVL comprises two protein fractions (i.e., LukF-PV corresponding to the fast-eluted F fraction and LukS-PV corresponding to the slow-eluted S fraction obtained by isolation via cation-exchange chromatography). LukF-PV and LukS-PV are inactive when they are present alone. However, they are characterized in that they cooperate to become active and exhibit cytolytic toxicity specific to human or rabbit polymorphonuclear leukocytes.

In addition to the above, it is also possible to use, as an immunogen, a recombinant LukF-PV or a recombinant LukS-PV produced by a genetic engineering technique.

Further, it is also possible to use, as an immunogen, a peptide fragment or a synthetic peptide obtained by treating the immunogen obtained above with a protease such as trypsin.

As an aside, PVL has a feature of exhibiting cytolytic toxicity specific to human or rabbit polymorphonuclear leukocytes. Known examples of a protein that exhibits leukocytolytic activity and is highly homologous to PVL include PVL variants LukD and LukE (FEBS Lett, 436, 202-208 (1998)), γ-hemolysin components HlgB and HlgC that exhibit moderate leukocytolytic activity and erythroclastic activity, and a γ-hemolysin component HlgA involved in erythroclasis (Infection and Immunity, October 1995, 4121-4129). Such highly homologous proteins can be obtained by a technique similar to the above technique and they can be used to confirm the reaction specificity of the antibody of the present invention.

Antibody Production

1. Polyclonal Antibodies

The polyclonal antibody specific to anti-LukF-PV and the polyclonal antibody specific to anti-LukS-PV of the present invention can be produced by the following method.

(1) Immunization Step

Mammals such as rabbits, mice, or rats are immunized with the use of the above purified LukF-PV and/or purified LukS-PV used as antigens. Administration is carried out by means of peritoneal injection, intravenous injection, subcutaneous injection, or the like, or in some cases, intradermal injection. After booster immunization is repeated several times, the mammals are subjected to blood sampling 3 to 10 days after the final immunization to obtain antisera (polyclonal antibodies).

(2) Production of Absorbed Antibodies

After antisera are obtained with the use of LukF-PV and/or LukS-PV in the above step, the antisera and LukF-PV or LukS-PV homologous proteins (LukF-PV homologous proteins LukD and HlgB and/or LukS-PV homologous proteins LukE, HlgC, and HlgA) are mixed together. Antibodies reacting with the homologous proteins are removed by absorption such that a polyclonal antibody (absorbed antibody) specific to a protein of interest can be produced. Such absorption operation makes it possible to obtain a polyclonal antibody specific to LukF-PV and a polyclonal antibody specific to LukS-PV (hereinafter, these antibodies are referred to as "specific polyclonal antibodies").

2. Monoclonal Antibodies

The monoclonal antibody capable of specifically recognizing and binding to LukF-PV (hereinafter referred to as "anti-LukF-PV monoclonal antibody") and the monoclonal antibody capable of specifically recognizing and binding to LukS-PV (hereinafter referred to as "anti-LukS-PV monoclonal antibody") of the present invention can be produced by a known method such as the Kohler and Milstein method (Kohler, G. and Milstein, C., Nature, 256, 495-497, 1975).

The above purified LukF-PV or purified LukS-PV can be used as an immunogen. It is desired that such an immunogen be administered with an appropriate adjuvant such as a commercially available Freund's complete adjuvant, Freund's incomplete adjuvant, BCG, aluminum hydroxide gel, or a pertussis vaccine. In addition, mice, rats, guinea pigs, and the like can be used as animals to be immunized, but usually mice are widely used. In the cases of mice, 3- to 10-week-old mice and preferably 4-week-old mice are used. A prepared immunogen can be subcutaneously, peritoneally, intravenously, intramuscularly, or intradermally administered to animals or via any possible route. Immunization intervals are not particularly limited; however, immunization is desirably carried out 2 to 5 times at 1 to 2 week intervals. Also, a single dose is not limited. For instance, an immunogen prepared as above can be mixed with an appropriate adjuvant and then several tens to several hundreds of micromililitters of the resultant can be administered.

3 to 10 days after the final immunization, antibody-producing cells are collected from immunized animals. Examples of antibody-producing cells include spleen cells, lymph node cells, thymic cells, and peripheral blood cells, but, in general, spleen cells are used. Spleens, lymph nodes, thymuses, peripheral blood, and the like are excised or collected from immunized animals and subjected to tissue disruption. The obtained disruptant is further suspended in a buffer solution such as PBS or a medium such as DMEM, RPMI-1640, or E-RDF and filtrated through 200- to 250-μm stainless mesh or the like, followed by centrifugation. Thus, antibody-producing cells of interest can be prepared.

The thus prepared antibody-producing cells are subjected to cell fusion with myeloma cells. For myeloma cells, established cell lines available to persons skilled in the art can be used. In general, myeloma cells used are obtained from an animal belonging to the species to which an immunized animal belongs. In some cases, those derived from a different species can be used. Preferably, a cell line to be used is a drug-resistant cell line characterized in that unfused cells thereof cannot survive in a selective medium such as a hypoxanthine-aminopterin-thymidine medium (HAT medium) while they can survive in such a medium only in a state of being fused with antibody-producing cells. In general, an 8-azaguanine-resistant cell line is used. This cell line lacks hypoxanthine-guanine phosphoribosyltransferase (HGPRT (−)) and thus cannot grow in an HAT medium. Examples of myeloma cells include cells of mice myeloma cell lines such as Sp2/O—Ag14 (ATCC CRL-1581; Nature, 276, 271 (1978)), P3X63Ag8 (ATCC TIB-9; Nature, 265, 495-497 (1978)), P3X63 Ag8U.1(P3U1) (ATCC CRL-1580; Current Topics in Microbiology and Immunology, 81, 1-7 (1978)), P3X63Ag8.653 (ATCC TIB-18; European J. Immunology, 6, 511-519 (1976)), and P2/NSI/1-Ag4-1 (ATCC CRL-1581; Nature, 276, 269-270 (1978)).

Cell fusion can be efficiently carried out by allowing myeloma cells and antibody-producing cells ($10^7$ to $10^8$ cells/ml) to come into contact with each other at a mixing ratio of 1:1 to 1:10 (e.g., 1:5) in an animal cell culture medium such as MEM, DMEM, RPMI-1640, or E-RDF in the presence of a fusion promoter at 30° C. to 37° C. for 1 to 3 minutes. As a fusion promoter, polyethylene glycol, polyvinyl alcohol, or the like, which has an average molecular weight of 1000 to 6000, can be used. Also, cell fusion can be carried out with the use of a fusion virus such as Sendai virus. Further, cell fusion can be carried out by a method using electrostimulation such as electroporation. A commercially available cell fusion apparatus using electroporation can be used.

Hybridomas can be selected from among cells subjected to cell fusion treatment by a method based on selective cell growth in a selective medium such as an HAT medium. For instance, a suspension containing fused cells is diluted with Iscove's medium (IMDM) containing an HAT supplement (Gibco BRL) and interleukin-6 (1 unit/mL) to a concentration of $10^3$ to $10^7$ cells/mL, followed by cell seeding at a cell density of $10^2$ to $10^6$ cells/well on a 96-well cell culture microplate. A selective medium such as an HAT medium is added to each well. Thereafter, cell culture is carried out, during which a selective medium is replaced with a fresh medium in an appropriate manner. Then, hybridomas are selected.

When cells of an 8-azaguanine-resistant cell line are used as myeloma cells and an HAT medium is used as a selective medium, unfused myeloma cells die approximately 7 to 10 days after culture. Also, antibody-producing cells, which are normal cells, cannot live in vitro for a long time, and they die approximately 7 to 10 days after culture. As a result, cells that have started to grow approximately 6 to 10 days after culture can be obtained as hybridomas.

The culture supernatant of grown cells is examined whether or not an antibody against LukF-PV or LukS-PV is produced therein. Then, a hybridoma capable of producing an antibody of interest is screened for. Screening for a hybridoma can be carried out by a usual method. For instance, a portion of a culture supernatant in a well in which hybridomas have grown is collected. Then, it is examined whether or not an antibody of interest is contained therein by enzyme immunoassay (EIA, ELISA), radioimmunoassay (RIA), or the like. For instance, a culture supernatant containing monoclonal antibodies is added to a 96-well microtiter plate to which purified LukF-PV or purified LukS-PV used as an immunogen is allowed to adsorb, allowing an antibody to react with an antigen.

Next, an enzyme-labeled anti-mouse immunoglobulin antibody is allowed to react with a specific antibody binding to an antigen and an enzyme substrate is added to each well for color development. Then, it is examined whether or not a monoclonal antibody in the culture supernatant reacts with immobilized purified LukF-PV or LukS-PV. In such case, examples of an enzyme used include β-D-galactosidase, peroxidase, alkaline phosphatase, and glucose oxidase. Color development can be detected with a signal reader appropriate for such assay, e.g., a microplate reader.

In the case of an anti-LukF-PV monoclonal antibody, primary screening is carried out in a manner such that a culture supernatant containing a monoclonal antibody that reacts with and binds to LukF-PV is selected. Further, secondary screening is carried out in a manner such that a culture supernatant containing a monoclonal antibody that does not react with a homologous protein is selected. Thus, a hybridoma that produces a monoclonal antibody capable of specifically recognizing LukF-PV can be screened for.

The reactivity to LukF-PV can be confirmed by, for example, enzyme immunoassay (EIA, ELISA) or an immunoblotting method (Western blot method) or in which purified LukF-PV is separated by polyacrylamide gel electrophoresis, a monoclonal antibody is allowed to react therewith, and color development caused by a labeled secondary antibody is observed.

Also, in the case of an anti-LukS-PV monoclonal antibody, it is possible to screen for a hybridoma that produces a monoclonal antibody capable of specifically recognizing LukS-PV in a similar manner.

Of the above selected hybridomas in a well, a hybridoma that produces a monoclonal antibody of interest is subjected to cloning. Cloning of the hybridoma can be carried out by a limiting dilution method, a soft agar method, a fibrin gel method, a cell sorter method for fluorescence excitation, or the like. Eventually, a hybridoma that produces a monoclonal antibody capable of specifically recognizing and binding to LukF-PV or LukS-PV can be obtained.

An anti-LukF-PV monoclonal antibody or an anti-LukS-PV monoclonal antibody (hereinafter to be referred to as a "specific monoclonal antibody") can be collected by a usual cell culture method with the use of a hybridoma that produces a monoclonal antibody capable of specifically recognizing LukF-PV or a hybridoma that produces a monoclonal antibody capable of specifically recognizing LukS-PV.

In a cell culture method, an anti-LukF-PV monoclonal antibody-producing hybridoma or an anti-LukS-PV monoclonal antibody-producing hybridoma is cultured in an animal cell culture medium such as IMDM, RPMI-1640, MEM, E-RDF, or a serum-free medium, which contains 10% to 20% calf or bovine fetal serum, under general culture conditions (e.g., 37° C., 5% $CO_2$ concentration) for 2 to 14 days. The antibody can be obtained from the culture supernatant. In an ascites method, a mineral oil such as pristane (2,6,10,14-tetramethylpentadecane) is peritoneally administered in advance to an animal belonging to the species to which a myeloma-cell-derived animal belongs. Then, anti-LukF-PV monoclonal antibody-producing hybridomas or anti-LukS-PV monoclonal antibody-producing hybridomas ($1 \times 10^7$ to $1 \times 10^9$ cells and preferably $5 \times 10^7$ to $1 \times 10^8$ cells) are peritoneally administered for mass production of the hybridomas. Ascites or blood is collected 1 to 4 weeks and preferably 2 to 3 weeks thereafter so that an antibody can be obtained.

In a case in which antibody purification is necessary, purification can be carried out by selecting one of or a combination of the following known methods or the like in an adequate manner: an ammonium-sulfate salting-out method; ion-exchange chromatography using an anion exchanger such as DEAE cellulose; molecular sieve chromatography wherein sieving is carried out based on molecular weight or structure; and hydroxyapatite chromatography.

As described above, the monoclonal antibody of the invention of the present application can be obtained. The monoclonal antibody may be a complete antibody or a fragment having an antibody-binding site such as Fab, Fab', F(ab')2, or Fv.

Also, the antibody of the present invention can be produced as a recombinant protein by isolating a gene encoding the antibody of the present invention from a hybridoma and carrying out a gene engineering technique. In particular, production using a gene engineering technique is appropriate for producing a humanized antibody and a human antibody. In such case, an antibody to be used as a medicine can be mass-produced.

The antibody of the present invention is an antibody against PVL obtained by the above method, which does not react with at least one of, and preferably does not react with all of, LukD, LukE, HlgB, HlgC, and HlgA. Further, the antibody of the present invention is an antibody that is capable of binding to LukF-PV and has no cross-reactivity to LukD and/or HlgB. Alternatively, it is an antibody that is capable of binding to LukS-PV and has no cross-reactivity to at least one of LukE, HlgC, and HlgA.

3. Antibody Labeling

When the antibody obtained by the above method is labeled to be used for a detection reagent, a labeling substance is not limited. Specific examples of a labeling substance that can be used include enzymes, radioisotopes, fluorescent dyes, biotin, dye sol, gold colloid, and insoluble carriers such as latex particles. In addition, labeling can be carried out by a known method.

4. PVL Detection

With the use of the thus obtained antibody that specifically reacts with LukF-PV or LukS-PV (LukF-PV and LukS-PV: binary (two components constituting) PVL), LukF-PV and/or LukS-PV can be detected in a *Staphylococcus aureus* culture supernatant.

Detection of LukF-PV and/or LukS-PV can be carried out by a method known to persons skilled in the art, such as an immunoblotting method, enzyme immunoassay (EIA, ELISA), radioimmunoassay (RIA), a fluorescent antibody method, a method using an agglutination reaction, and immunochromatography. Upon detection, a culture product that can be used as a sample is, for example, a culture supernatant of *Staphylococcus aureus*, which is a clinical bacterial isolate derived from a different clinical test sample, but it is not limited thereto.

For instance, with the use of a carrier sensitized with a polyclonal or monoclonal antibody that specifically recognizes LukF-PV, LukF-PV can be detected by an agglutination method or EIA. Also, LukS-PV can be detected in a similar manner.

In the case of an agglutination method, any carrier may be used as a carrier sensitized with such a specific polyclonal or monoclonal antibody, as long as it is an insoluble and stable carrier that does not induce a non-specific reaction. For example, latex particles, bentonite, collodion, kaolin, fixed sheep red blood cells, and the like can be used, but latex particles are preferably used. Examples of latex particles that can be used include polystyrene latex particles, styrene-butadiene copolymer latex particles, and polyvinyl toluene latex particles, but polystyrene latex particles are preferably used. The use of latex particles is further advantageous in that a carrier can be readily sensitized with an antibody without a special treatment and that a clear agglutination image that is generated upon a reaction of a sample and a carrier can be obtained such that reactivity of the sample to the carrier can be readily determined with good accuracy.

A method for allowing a specific polyclonal antibody or a specific monoclonal antibody to sensitize a carrier is not particularly limited. For instance, a specific polyclonal antibody or a specific monoclonal antibody is allowed to physically adsorb or chemically bind to a carrier. More specifically, for instance, specific polyclonal antibodies or specific monoclonal antibodies are mixed with carriers and the resultant is subjected to heating and shaking at 30° C. to 37° C. for 1 to 2 hours, such that the antibodies are allowed to sensitize carriers. The amount of antibodies that sensitize carriers can be adequately determined in accordance with the particle sizes of carriers to be used. After allowing antibodies to sensitize carriers, it is preferable to block unsensitized portions on the carrier surfaces with bovine serum albumin, human serum albumin, rabbit serum albumin, albumen, or the like. Preferably, the carriers sensitized with specific polyclonal antibodies or specific monoclonal antibodies are maintained in a medium dispersion solution until they are allowed to react with a sample. In such case, examples of a medium that can be used include phosphate buffer and glycine buffer. The content of carriers sensitized with specific polyclonal antibodies or specific monoclonal antibodies is generally 0.2% to 0.5% by weight and preferably 0.25% to 0.3% by weight with respect to the weight of the medium dispersion solution. According to need, bovine serum albumin, gelatin, gum Arabic, or the like may be added to the medium. The thus prepared carriers sensitized with specific polyclonal antibodies or specific monoclonal antibodies are allowed to react with a sample. Then, the reactivity of a sample to a specific polyclonal antibody or a specific monoclonal antibody can be determined in accordance with the occurrence or nonoccurrence of agglutination or the extent of agglutination. Thus, LukF-PV or LukS-PV can be detected.

In addition, in the case of enzyme immunoassay (EIA), in order to detect LukF-PV, a polyclonal antibody or an anti-LukF-PV monoclonal antibody that is capable of specifically recognizing LukF-PV is immobilized on a carrier such as a microtiter plate, a resin bead, or a magnetic bead via physical adsorption or chemical binding. In order to detect LukS-PV, a polyclonal antibody or an anti-LukS-PV monoclonal antibody that is capable of specifically recognizing LukS-PV is immobilized on a carrier such as a microtiter plate, a resin bead, or a magnetic bead via physical adsorption or chemical binding.

The amounts of antibodies immobilized are not particularly limited. However, in a case in which a carrier is a microtiter plate, the amount per well is preferably several nanograms to several tens of micrograms. Immobilization can be carried out by dissolving antibodies to be immobilized in an appropriate buffer such that the antibodies come into contact with carriers. For example, in a case in which microtiter wells are used, immobilization can be carried out in a manner such that an antibody solution is dispensed in each well of a microtiter plate and allowed to stand for a certain period of time. After immobilizing a substrate, it is preferable to carry out blocking with the use of a blocking solution containing bovine serum albumin, human serum albumin, rabbit serum albumin, albumen, or the like, in order to prevent non-specific binding during assay. Subsequently, the immobilized carrier and a sample are allowed to react with each other, followed by washing. Then, in order to detect LukF-PV, a labeled polyclonal antibody capable of specifically recognizing LukF-PV or a labeled anti-LukF-PV monoclonal antibody is allowed to react therewith. Also, in order to detect LukS-PV, a labeled polyclonal antibody capable of specifically recognizing LukS-PV or a labeled anti-LukS-PV monoclonal antibody is allowed to react therewith. Labeling can be carried out using an enzyme such as β-D-galactosidase, peroxidase, alkaline phosphatase, or glucose oxidase.

For instance, in the case of enzyme immunoassay (ELISA), a substrate is immobilized on a multiple-well (e.g. 96-well) microtiter plate and an antigen-antibody reaction is induced in wells, such that simultaneous mass assay is achieved. In addition, the amounts of antibodies and a sample to be used can be significantly reduced. Further, an automatic analyzer such as a fully-automatic EIA analyzer can also be used.

It is an objective of the present invention to provide a kit whereby PVL produced by *Staphylococcus aureus* can be detected. The kit comprises at least one antibody selected from among a monoclonal antibody capable of specifically recognizing LukF-PV, a monoclonal antibody capable of specifically recognizing LukS-PV, a polyclonal antibody capable of specifically recognizing LukF-PV, and a polyclonal antibody capable of specifically recognizing LukS-PV.

When the kit is applied to an EIA method, it may comprise a carrier on which antibodies are immobilized, or a carrier to which antibodies have bound in advance may be used. When the kit is applied to an agglutination method using a carrier such as a latex, it may comprise an antibody-adsorbed carrier. In addition, the kit may adequately comprise a blocking solution, a reaction solution, a reaction termination solution, a reagent with which a sample is treated, and the like.

As described above, PVL produced by *Staphylococcus aureus* can be detected with the use of at least one antibody selected from among the anti-LukF-PV monoclonal antibody, the anti-LukS-PV monoclonal antibody, the polyclonal antibody capable of specifically recognizing LukF-PV, and the polyclonal antibody capable of specifically recognizing LukS-PV of the present invention.

The antibody of the present invention is a neutralizing antibody capable of removing or attenuating PVL toxicity and inhibiting PVL leukocytolytic toxin activity.

The neutralizing antibody titer of the antibody of the present invention can be determined by obtaining the fatality or incidence of a disease affecting an animal such as a mouse to which the antibody of the present invention has been administered with PVL-producing *Staphylococcus aureus* or purified PVL toxin. The order for administering the antibody of the present invention and PVL-producing *Staphylococcus aureus* or purified PVL toxin is not limited, and thus they may be simultaneously administered. The neutralizing antibody titer can be determined by administering the antibody to a plurality of animal individuals and counting the number of living animals or unaffected animals. In such case, a control animal group is prepared by administering PVL-producing *Staphylococcus aureus* or purified PVL toxin alone to animals without administering the antibody of the present invention thereto. Accordingly, effects of the antibody of the present invention can be determined by comparing the group treated with PVL-producing *Staphylococcus aureus* or purified PVL toxin and the untreated control group.

In addition, purified PVL toxin and the antibody of the present invention are mixed and the resultant is further mixed with human blood (preferably granulocyte fraction and more preferably neutrophil fraction) to which an anticoagulant such as heparin has been added or with rabbit blood (preferably granulocyte fraction and more preferably neutrophil fraction) to which an anticoagulant such as heparin has been added, followed by reaction for a certain period of time. Subsequently, the number of leukocytes disintegrated due to PVL activity (preferably the number of granulocytes and more preferably the number of neutrophils) is determined. In such case, a control group treated with the PVL toxin alone without the antibody of the present invention is prepared. Accordingly, effects of the antibody of the present invention can be determined by comparing the group treated with the above mixture containing purified PVL toxin and the group treated with purified PVL toxin alone.

Furthermore, the antibody of the present invention has effects of neutralizing a recombinant LukF-PV and/or a recombinant LukS-PV produced in the present invention and effects of inhibiting the activity of PVL, which is a leukocytolysis factor produced by *Staphylococcus aureus*. Thus, it can be used as a pharmaceutical product and as an agent for preventing/treating a PVL-caused disorder that may result in serious conditions due to infection with PVL toxin-producing *Staphylococcus aureus* or PVL toxin. Examples of a PVL-caused disorder include leukocytolysis.

Preferably, the pharmaceutical composition of the present invention contains a physiologically acceptable diluent or carrier, in addition to the antibody of the present invention. Also, it may be a mixture containing another antibody or a drug, such as an antibiotic. Examples of an appropriate carrier include, but are not limited to, a physiological saline solution, a phosphate buffer physiological saline solution, a phosphate buffer physiological saline-glucose solution, and a physiological saline buffer solution. The pharmaceutical composition of the present invention can be administered by an oral route or a parenteral route. For example, it can be injected intravenously, intramuscularly, subcutaneously, or peritoneally. The effective dose of the antibody of the present invention and the effective dose of the antibody of the present invention that is administered in combination with an appropriate diluent and a pharmacologically usable carrier are preferably 0.0001 mg to 100 mg/kg by body weight for a single administration.

The pharmaceutical composition of the present invention includes, for example, an anti-PVL toxin vaccine comprising, as an active ingredient, the antibody of the present invention.

EXAMPLES

The present invention is hereafter described in greater detail with reference to the following examples, although the technical scope of the present invention is not limited thereto.

Example 1

Production of Immunogens

A recombinant LukF-PV and a recombinant LukS-PV were prepared by the method described below.

A *Staphylococcus aureus* MW2 strain (MW2 strain), which is a PVL-gene-positive strain, was subjected to shaking culture in an LB medium (4 mL) at 37° C. for 20 hours under aerobic conditions. The MW2 strain chromosomal DNA was extracted from the culture solution with the use of an ISOPLANTII DNA extraction kit (NIPPON GENE).

In order to extract the gene of interest for recombinant production, primers were prepared based on total nucleotide sequence information (LANCET 2002; 359:1819-1827). Further, in order to prevent mixing and amplification of non-specific PCR products, the nucleotide sequence encoding the amino acid sequence of a recombinant LukF-PV (903 b.p) and the nucleotide sequence encoding the amino acid sequence of a recombinant LukS-PV (855 b.p) were extracted by two-stage PCR. The first PCR amplification was carried out using the MW2 strain chromosomal DNA as template DNA such that a DNA fragment comprising the nucleotide sequence encoding LukF-PV (1620 b.p) and a DNA fragment comprising the nucleotide sequence encoding LukS-PV (1642 b.p) were obtained. Each DNA fragment was separated by 1.5% agarose gel electrophoresis. Then, each purified DNA fragment was extracted from isolation gel with the use of a High Pure PCR Product Purification Kit (Roche).

Subsequently, a primer for the addition of a restriction enzyme BamHI recognition sequence and a primer for the addition of a restriction enzyme SalI recognition sequence were designed for the 5' end and the 3' end of a DNA fragment, respectively. The $2^{nd}$ PCR amplification was carried out using, as template DNA, a PCR purified product obtained as a result of the first PCR. A DNA fragment encoding the amino acid sequence of the recombinant LukF-PV and containing the restriction enzyme recognition sites (925 b.p with the restriction enzyme recognition sites) and a DNA fragment encoding the amino acid sequence of the recombinant LukS-PV and containing the restriction enzyme recognition sites (877 b.p with the restriction enzyme recognition sites) were obtained.

The DNA fragments were used for transformation of *Escherichia coli* JM109 according to a conventional method. Each obtained transformant was cultured in an LB medium (250 ml) containing ampicillin (100 µg/ml) at 37° C. When the O.D. unit (optical density at 550 nm) was 0.4 to 0.8, 1M IPTG was added thereto to a concentration of 1 mM and culture was further continued for 3 hours. The cell culture solution was centrifuged at 10000 rpm for 2 minutes for cell harvest. The resultant was suspended in 10 ml of a buffer solution (50 mM Tris-HCl (pH 8.0), 0.1 M NaCl, 20% Glycerol, 0.1% TritonX-100, 1 mM mercaptoethanol, 1 mM EDTA, 1 mg/mL Lysozyme, and 2 mM PMSF). Cells were disintegrated by ultrasonic disruption for 15 minutes. The LukF-PV protein and the LukS-PV protein expressed in cells were purified. Thus, a recombinant LukF-PV (purified LukF-PV, 35 kDa) and a recombinant LukS-PV (purified LukS-PV, 31 kDa) were produced.

Also, in the cases of the homologous proteins LukD and HlgB, which are highly homologous to LukF-PV, a recombinant LukD (purified LukD, 35 kDa) and a recombinant HlgB (purified HlgB, 35 kDa) were obtained. In addition, also in the cases of the homologous proteins LukE, HlgC, and HlgA, which are highly homologous to LukS-PV, a recombinant LukE (purified LukE 31 kDa), a recombinant HlgC (purified HlgC, 31 kDa), and a recombinant HlgA (purified HlgA, 31 kDa) were obtained in a similar manner.

Example 2

Production of Polyclonal Antibodies

In order to obtain a polyclonal antibody against LukF-PV, the purified LukF-PV (50 µg) produced in Example 1 and Freund's complete adjuvant were mixed, and the mixture was subcutaneously injected into a rabbit for immunization. Further, for booster immunization, the purified LukF-PV (100 µg) and a Freund's incomplete adjuvant were mixed, and the mixture was subcutaneously injected into the rabbit twice in total at a 2-week interval. For another booster immunization, the purified LukF-PV (50 µg) was intravenously injected into the rabbit twice in total at a 2-week interval. On day 5 after the final immunization, the immunized rabbit was subjected to exsanguination such that the anti-LukF-PV serum was obtained.

In addition, in order to obtain a polyclonal antibody against LukS-PV, purified LukS-PV (50 µg) and Freund's complete adjuvant were mixed, and the mixture was subcutaneously injected into a rabbit for immunization. Further, for booster immunization, the purified LukS-PV (100 µg) and Freund's incomplete adjuvant were mixed, and the mixture was subcutaneously injected into the rabbit twice in total at a 2-week interval. For another booster immunization, the purified LukS-PV (50 µg) was intravenously injected into the rabbit twice in total at a 2-week interval. On day 5 after the final immunization, the immunized rabbit was subjected to exsanguination such that the anti-LukS-PV serum was obtained.

Next, the reactivity of each antibody was confirmed by Western blotting.

In order to confirm an antibody against LukF-PV, purified LukF-PV (20 ng), purified LukD (20 ng), and purified HlgB (20 ng) were fractionated by SDS polyacrylamide gel electrophoresis and transcribed to a PVDF membrane (Immun-Blot PBDF Membrane, 0.2 µm, BIO-RAD). In order to confirm an antibody against LukS-PV, purified LukS-PV (10 ng), purified LukE (10 ng), purified HlgC (10 ng), and purified HlgA (10 ng) were fractionated by SDS polyacrylamide gel electrophoresis and transcribed to a PVDF membrane (Immun-Blot PVDF Membrane, 0.2 µm, BIO-RAD).

After transcription, in order to block non-specific binding sites, each PVDF membrane was incubated overnight at 4° C. with a PBS solution containing 5% skimmed milk and 0.25% Tween20. Next, each membrane was washed 3 times with PBS (TPBS) containing 0.25% Tween20 and then mixed with the corresponding antiserum diluted with TPBS (1:250), followed by incubation at room temperature for 1 hour, resulting in a primary antibody reaction. Then, each membrane was washed 3 times with TPBS and incubated at room temperature for 1 hour with an alkaline phosphatase-labeled anti-rabbit IgG (whole molecule) goat antibody (Sigma) diluted with TPBS (1:10,000). Eventually, antibody reactivity was confirmed by a chromogenic reaction. The chromogenic reaction reagent used was an AP Conjugate Substrate Kit (BIO-RAD).

As a result of confirmation of the reactivity of the anti-LukF-PV serum by the Western blotting method, it was shown that the anti-LukF-PV serum reacts not only with purified LukF-PV but also with the purified homologous proteins LukD and HlgB. Table 1 shows the results. Criteria used in the table are described below.

Criterion (+): Reactivity confirmed between antigen protein and antibody (antiserum)

Criterion (−): No reactivity confirmed between antigen protein and antibody (antiserum)

TABLE 1

|  | LukF-PV | LukD | HlgB |
|---|---|---|---|
| Anti-LukF-PV serum | + | + | + |

In addition, as a result of confirmation of the reactivity of the anti-LukS-PV serum by the Western blotting method, it was shown that the anti-LukS-PV serum reacts not only with purified LukS-PV but also with the purified homologous proteins LukE, HlgC, and HlgA. Table 2 shows the results. Criteria used in the table are described below.

Criterion (+): Reactivity confirmed between antigen protein and antibody (antiserum)

Criterion (−): No reactivity confirmed between antigen protein and antibody (antiserum)

TABLE 2

|  | LukS-PV | LukE | HlgC | HlgA |
|---|---|---|---|---|
| Anti-LukS-PV serum | + | + | + | + |

Example 3

Removal of Cross-Reactivity Between LukF-PV and LukS-PV

In order to provide a polyclonal antibody specific to LukF-PV and a polyclonal antibody specific to LukS-PV, an absorption operation was carried out to remove the confirmed reactivity to LukD and that to HlgB from the anti-LukF-PV serum and also to remove the confirmed reactivity to LukE, that to HlgC, and that to HlgA from the anti-LukS-PV serum.

For production of a column used for the absorption operation, Formyl-Cellulofine (Seikagaku Corporation) was used as a carrier. For the anti-LukF-PV serum, purified LukD and purified HlgB were used as ligands for absorption. For the anti-LukS-PV serum, purified LukE, purified HlgC, and purified HlgA were used as ligands for absorption. Columns were prepared by allowing a different ligand to bind to a single column in accordance with the method described in "Cellulofine Affinity Chromatography" published by Seikagaku Corporation.

For absorption of anti-LukF-PV serum, an anti-LukF-PV serum diluted 10-fold with PBS was added to an HlgB column such that the reactivity to HlgB contained in the anti-LukF-PV serum was removed by adsorption. Then, the antiserum was added to a LukD column such that the reactivity to LukD contained in the anti-LukF-PV serum was removed by adsorption. The reactivity to HlgB and that to LukD were removed from the anti-LukF-PV serum such that an absorbed serum (hereinafter referred to as "absorbed serum F") capable of specifically recognizing LukF-PV was prepared. Likewise, an anti-LukS-PV serum was diluted 10-fold with PBS. Then, the resultant was added to a, HlgC column, a LukE column, and then to an HlgA column such that the reactivity to HlgC, that to LukE, and that to HlgA were removed from the anti-LukS-PV serum. Thus, an absorbed serum (hereinafter referred to as "absorbed serum S") capable of specifically recognizing LukS-PV was produced.

The reactivity of the absorbed serum F was confirmed by the Western blotting method in a manner similar to that used in Example 2. As a result, the absorbed serum F had reactivity to purified LukF-PV; however, it was not confirmed to have reactivity to the purified LukF-PV homologous proteins LukD or HlgB. The results indicate that the absorbed antiserum F does not react with LukD or HlgB but specifically reacts with LukF-PV, and that the specificity of an absorbed antibody has been improved according to the present invention.

Table 3 shows the results. Criteria used in the table are described below.

Criterion (+): Reactivity confirmed between antigen protein and antibody (antiserum)

Criterion (−): No reactivity confirmed between antigen protein and antibody (antiserum)

TABLE 3

|  | LukF-PV | LukD | HlgB |
|---|---|---|---|
| Absorbed serum F | + | − | − |

In addition, the reactivity of the absorbed serum S was confirmed by the Western blotting method in a manner similar to that used in Example 2. As a result, the absorbed serum S had reactivity to purified LukS-PV; however, it was not confirmed to have reactivity to the purified LukS-PV homologous proteins LukE, HlgC, and HlgA. The results indicate that the absorbed serum S does not react with LukD, HlgC, or HlgA but specifically reacts with LukS-PV, and that the specificity of an absorbed antibody has been improved according to the present invention.

Table 4 shows the results. Criteria used in the table are described below.

Criterion (+): Reactivity confirmed between antigen protein and antibody (antiserum)

Criterion (−): No reactivity confirmed between antigen protein and antibody (antiserum)

TABLE 4

|  | LukS-PV | LukE | HlgC | HlgA |
|---|---|---|---|---|
| Absorbed serum S | + | − | − | − |

Based on the above results, a polyclonal antibody specific to LukF-PV and a polyclonal antibody specific to LukS-PV were obtained.

Example 4

Production of Monoclonal Antibodies

Production of Anti-LukF-PV Monoclonal Antibodies

A 5-week-old female BALB/c mouse was immunized with purified LukF-PV (100 μg) serving as an immunogen and Freund's complete adjuvant. Two weeks later, booster immunization was carried out with the same antigen (50 μg) and Freund's incomplete adjuvant. Another two weeks later, the same antigen (25 μg) was intravenously injected into the mouse. Three days later, spleen cells were excised. The excised spleen cells were fused with mouse myeloma cells (P3X63-Ag8.653) by the method of Kohler et al., (Kohler et al., Nature, vol. 256, pp. 495-497 (1975)), followed by culture in a carbonic acid gas incubator at 37° C. The obtained hybridoma culture supernatant as a specimen was subjected to hybridoma screening by a solid-phase ELISA method with the use of purified LukF-PV as an antigen. Then, hybridomas in a culture supernatant in which a reaction had been observed were selected.

All screened hybridomas were seeded on a 96-well plate to 1.5 cells per well by limiting dilution. Hybridomas that had grown and formed a single colony in a well were designated as clones. The above limiting dilution was repeated twice for cloning.

Accordingly, five monoclonal antibody-producing cell lines capable of recognizing purified LukF-PV (LukF-PV E-16-5M, LukF-PV E-26-2M, LukF-PV G-1-2M, LukF-PV 2F-9-2M, and LukF-PV 2F-9-4M) were obtained. The obtained cell lines were peritoneally administered to pristine-treated BALB/c mice. Approximately 2 weeks later, antibody-containing ascites was collected.

Further, ascites samples were prepared by diluting 1000-fold the ascites obtained as a result of each instance of primary screening with PBS. The ELISA test was carried out according to a conventional method with the use of plates on which purified LukF-PV, purified LukD, and purified HlgB antigens had been immobilized at a concentration of 0.1 μg per well, 0.3 mg/mL 3,3′,5,5′-tetramethylbenzidine (containing 0.0075 vol % hydrogen peroxide) as a substrate solution, and a reaction termination solution (0.3 mol/L sulfuric acid) for absorbance measurement (observed wavelength: 450 nm; reference wavelength: 630 nm). Regarding specificity criteria, a sample showing an absorbance of 0.2 or more was determined to be a positive sample (reactivity: +) and a sample showing an absorbance of 0.2 or less was determined to be a negative sample (reactivity: −).

The monoclonal antibodies produced by the hybridomas (LukF-PV G-1-2M and LukF-PV 2F-9-4M) were confirmed to have reactivity to purified LukF-PV but not to have reactivity to the purified homologous proteins LukD and HlgB. Table 5 lists the results.

TABLE 5

|  |  | Antigen type | | |
|---|---|---|---|---|
|  |  | LukF-PV | LukD | HlgB |
| Ascites LukF-PV G-1-2M | Absorbance | 0.363 | 0.075 | 0.051 |
|  | Reactivity | + | − | − |
| Ascites LukF-PV 2F-9-4M | Absorbance | 0.627 | 0.084 | 0.029 |
|  | Reactivity | + | − | − |

Preparation of Anti-LukS-PV Monoclonal Antibodies

As described above, 9 different monoclonal antibody-producing cell lines capable of recognizing purified LukS-PV (LukS-PV A-2-1M, LukS-PV A-2-4M, LukS-PV B-10-2M, LukS-PV B-10-3M, LukS-PV D-6-1M, LukS-PV D-6-2M, LukS-PV D-14-9M, LukS-PV 2G-5-2M, and LukS-PV 2G-5-4M) were obtained. The obtained cell lines were peritoneally administered to pristane-treated BALB/c mice. Approximately 2 weeks later, antibody-containing ascites was collected.

Subsequently, ascites samples were prepared by diluting 1000-fold the ascites obtained as a result of each instance of primary screening with PBS. The ELISA test was carried out according to a conventional method with the use of plates on which purified LukS-PV, purified LukE, purified HlgC, and purified HlgA antigens had been immobilized at a concentration of 0.1 μg per well, 0.3 mg/mL 3,3′,5,5′-tetramethylbenzidine (containing 0.0075 vol % hydrogen peroxide) as a substrate solution, and a reaction termination solution (0.3 mol/L sulfuric acid) for absorbance measurement (observed wavelength: 450 nm; reference wavelength: 630 nm). Regarding specificity criteria, a sample showing an absorbance of 0.2 or more was determined to be a positive sample (reactivity: +) and a sample showing an absorbance of 0.2 or less was determined to be a negative sample (reactivity: −).

The monoclonal antibodies produced by the hybridomas (LukS-PV B-10-2M and LukS-PV D-14-9M) were confirmed to have reactivity to purified LukS-PV but not to have reactivity to the purified homologous proteins LukE, HlgC, and HlgA. Table 6 lists the results.

TABLE 6

|  |  | Antigen type | | | |
| --- | --- | --- | --- | --- | --- |
|  |  | LukS-PV | LukE | HlgC | HlgA |
| Ascites LukS-PV B-10-2M | Absorbance | 0.398 | 0.022 | 0.029 | 0.047 |
|  | Reactivity | + | − | − | − |
| Ascites LukS-PV D-14-9M | Absorbance | 0.438 | 0.029 | 0.036 | 0.057 |
|  | Reactivity | + | − | − | − |

Example 5

Immunological Detection Method

An anti-LukF-PV antibody was purified by a conventional method from the absorbed serum F containing an antibody capable of specifically binding to LukF-PV obtained in Example 3. Then, an anti-LukF-PV antibody-sensitized latex (sensitized latex F) was prepared by a conventional method with the use of the anti-LukF-PV antibody and spherical polystyrene particles 0.8 μm in diameter as supports.

Also, an anti-LukS-PV antibody was purified from the absorbed serum S containing an antibody capable of specifically binding to LukS-PV obtained in Example 3. Then, an anti-LukS-PV antibody sensitized latex (sensitized latex S) was prepared in a similar manner.

In addition, in order to confirm the above reagents, standard toxins were prepared. For the sensitized latex F, purified LukF-PV used as an immunogen was adjusted to 100 ng/mL such that a standard toxin LukF-PV was obtained. For the sensitized latex S, purified LukS-PV used as an immunogen was adjusted to 100 ng/mL such that a standard toxin LukS-PV was obtained.

Example 6

Evaluation of PVL Detection Reagents in *Staphylococcus aureus* Culture Supernatants 35 PVL-gene-positive *Staphylococcus aureus* strains and 29 PVL-gene-negative *Staphylococcus aureus* strains (JOURNAL OF CLINICAL MICROBIOLOGY, November, 2002, pp. 4289-4294, etc.) were used as test strains and the culture supernatants thereof were used as specimens for PVL detection. The detection was carried out by a reversed passive latex agglutination reaction (the RPLA method) with the use of the reagents that were the sensitized latex F and the sensitized latex S produced in Example 5. FIG. 1 lists the names of test strains.

For culture supernatant preparation, 3 mL of a CCY modified medium (Res. Microbiol. 1991, 142, 75-85) was inoculated with a different test strain, followed by shaking culture at 37° C. for 24 hours at 130 rpm. The supernatant of each culture solution was collected by centrifugation. The obtained culture supernatants were used as samples.

Upon testing, the culture supernatants, the sensitized latex F and the sensitized latex S prepared in Example 5, a V-bottom 96-well microplate, a buffer solution (included in a commercially available *Staphylococcus* enterotoxin detection kit SET-RPLA "SEIKEN:" Denka Seiken Co., Ltd.), a standard toxin LukF-PV, and a standard toxin LukS-PV were used.

In the test method, two arrays (1 array: 8 wells) of a microplate were used for each specimen for LukF-PV detection and LukS-PV detection. A buffer solution (25 μL) was added to every well and a sample (25 μL) was added to the first well (the $1^{st}$ well) (2-fold dilution). Further, 25 μL of the 2-fold diluted sample in the first well was aspirated and used for 2-fold serial dilution in the following wells excluding the last well (the $8^{th}$ well). As a result of such serial dilution, the specimen was diluted with the buffer solution at ratios of 1:2 to 1:128. The last well was used for a negative control of the relevant latex reagent. The sensitized latex F (25 μL) was added dropwise to 8 wells of an array for LukF-PV detection and the sensitized latex S (25 μL) was added dropwise to 8 wells of an array for LukS-PV detection, followed by mixing of the specimen and the reagent with a microplate mixer. In order to avoid evaporation of the reaction solution, the microplate was placed in a moist chamber and allowed to stand for 24 hours at room temperature, followed by determination. Each test strain culture supernatant was subjected to the above operation.

A supernatant was determined to be PVL positive (PVL-detected) in a case in which an agglutination titer of sensitized latex F to LukF-PV of 1:2 or more and that of sensitized latex S to LukS-PV of 1:2 or more were confirmed by the test according to the method of the present invention. PVL was detected in the culture supernatants of all the 35 test strains that had been found to be PVL-gene-positive by the PCR method. In addition, the culture supernatants of all the 29 test strains that had been found to be PVL-gene-negative by the PCR method were found to be PVL-negative upon detection. FIGS. 2A and 2B show the results. In the present invention, positive results for PVL detection are represented by "+" and negative results for PVL detection are represented by "−."

In addition, each standard toxin prepared in Example 5 was allowed to react with the corresponding sensitized latex such that the reagent sensitivity and the occurrence of natural agglutination were confirmed.

Each standard toxin (100 ng/mL) was tested with specimens subjected to 2-fold serial dilution. Accordingly, agglutination was observed at an agglutination titer of sensitized latex F to standard toxin LukF-PV of up to 1:32 and at an agglutination titer of sensitized latex S to standard toxin LukS-PV of up to 1:32. The results are summarized in table 7. In addition, criteria used in the table are as follows.

Criterion (+): Agglutination observed (agglutination level: +++>++>+)
Criterion (−): No agglutination observed

TABLE 7

| | Standard toxin LukF-PV (100 ng/mL) | | | | | | |
|---|---|---|---|---|---|---|---|
| | 1:2 50 ng/mL | 1:4 25 ng/mL | 1:8 12.5 ng/mL | 1:16 6.3 ng/mL | 1:32 3.2 ng/mL | 1:64 1.6 ng/mL | 1:128 0.8 ng/mL |
| Sensitized latex F | +++ | +++ | +++ | +++ | ++ | + | − |
| Sensitized latex S | +++ | +++ | +++ | +++ | ++ | + | − |

The results obtained by the PCR method correspond to the detection results obtained with the use of the reagents of the present invention at a match rate of 100% (and at a non-match rate of 0%). FIG. 3 shows the results. In FIG. 3, in a case in which an agglutination titer of 1:2 or more was confirmed for both sensitized latex F and sensitized latex S, a specimen culture supernatant was determined to be PVL-positive upon detection. This revealed that PVL can be specifically detected with high sensitivity by the method of the present invention.

Example 7

Neutralizing Activity Evaluation

The PVL neutralizing activity of the anti-LukF-PV antibody and that of the anti-LukS-PV antibody were determined.

The anti-LukF-PV serum (100 μL) prepared in Example 2 and the purified LukF-PV (30 μg/50 μL) were mixed so as to react with each other at 4° C. for 16 hours such that a neutralized toxin was obtained. In addition, PBS (100 μL) and purified LukF-PV (30 μg/50 μL) were mixed such that a system free from antiserum action was obtained as a comparative control.

Likewise, the anti-LukS-PV serum (100 μL) prepared in Example 2 and the purified LukS-PV (30 μg/50 μL) were mixed so as to react with each other at 4° C. for 16 hours such that a neutralized toxin was obtained. In addition, PBS (100 μL) and purified LukS-PV (30 μg/50 μL) were mixed such that a system free from antiserum action was obtained as a comparative control.

Each above neutralized toxin (10 μg) or control toxin (10 μg) was added to human venous blood (1 mL) mixed with heparin capable of acting as a coagulant at the relevant composition shown in table 8, followed by incubation at 37° C. for 90 minutes. Then, the number of neutrophils was determined.

TABLE 8

| Condition | Human blood | LukF-PV Toxin | LukF-PV Antiserum | LukS-PV Toxin | LukS-PV Antiserum | PBS | Total |
|---|---|---|---|---|---|---|---|
| Addition of neutralized toxin | 1 mL | 10 μg | 33.3 μL | 10 μg | 33.3 μL | 33.4 μL | 1.1 mL |
| Addition of toxin (unneutralized) | 1 mL | 10 μg | 0 | 10 μg | 0 | 100 μL | 1.1 mL |
| Addition of serum alone (control) | 1 mL | 0 | 33.3 μL | 0 | 33.3 μL | 33.4 μL | 1.1 mL |
| Addition of PBS alone (control) | 1 mL | 0 | 0 | 0 | 0 | 100 μL | 1.1 mL |

An automated multi-item hematology analyzer SFVU-1 (Sysmex Corporation) was used to determine the number of neutrophils.

In control systems to each of which a toxin was not added, the numbers of neutrophils contained in 1 μL of blood after reaction were 2565 cells and 2695 cells.

In addition, the number of neutrophils obtained after mixing of an unneutralized toxin followed by reaction was determined to be 470 cells in 1 μL of blood subjected to reaction. This indicated that the recombinant LukF-PV and the recombinant LukS-PV produced in the steps of the present invention have leukocytolytic activity. Further, in a system in which toxins obtained by mixing the above active toxins with the corresponding antiserums for neutralizing treatment were allowed to react, the number of neutrophils was determined to be 2890 cells in 1 μL of blood subjected to reaction. This indicated that the leukocytolytic activity was inhibited. Table 9 shows the results.

TABLE 9

| Condition | Number of neutrophils | Reaction condition | | | | | | |
|---|---|---|---|---|---|---|---|---|
| | | Human blood | LukF-PV Toxin | LukF-PV Antiserum | LukS-PV Toxin | LukS-PV Antiserum | PBS | Total |
| Addition of neutralized toxin | 2890 | 1 mL | 10 μg | 33.3 μL | 10 μg | 33.3 μL | 33.4 μL | 1.1 mL |
| Addition of toxin (unneutralized) | 470 | 1 mL | 10 μg | 0 | 10 μg | 0 | 100 μL | 1.1 mL |
| Addition of serum alone (control) | 2695 | 1 mL | 0 | 33.3 μL | 0 | 33.3 μL | 33.4 μL | 1.1 mL |
| Addition of PBS alone (control) | 2565 | 1 mL | 0 | 0 | 0 | 0 | 100 μL | 1.1 mL |

All publications, patents, and patent applications cited herein are incorporated herein by reference in their entirety.

The invention claimed is:

1. An isolated antibody capable of binding to Panton-Valentine leukocidin F (LukF-PV), wherein the isolated antibody does not specifically cross-react with at least one homologous protein of LukF-PV selected from the group consisting of LukD and HlgB.

2. An isolated antibody capable of binding to Panton-Valentine leukocidin F (LukF-PV), wherein the isolated antibody inhibits leukocytolytic toxin activity and does not specifically cross-react with at least one homologous protein of LukF-PV selected from the group consisting of LukD and HlgB.

3. A Panton-Valentine leukocidin detection kit comprising the isolated antibody according to claim 1.

4. A Panton-Valentine leukocidin detection kit comprising the isolated antibody according to claim 2.

* * * * *